United States Patent
Silverman et al.

(10) Patent No.: US 8,465,457 B2
(45) Date of Patent: Jun. 18, 2013

(54) MINIMIZING RESISTANCE TO CATHETER ADVANCEMENT DURING VASCULAR CANNULATION

(76) Inventors: David G. Silverman, West Redding, CT (US); Sally A. Kniffin, Redding, CT (US)

(*) Notice: Subject to any disclaimer, the term of this patent is extended or adjusted under 35 U.S.C. 154(b) by 0 days.

(21) Appl. No.: 13/314,885

(22) Filed: Dec. 8, 2011

(65) Prior Publication Data
US 2012/0150121 A1    Jun. 14, 2012

Related U.S. Application Data

(60) Provisional application No. 61/421,135, filed on Dec. 8, 2010.

(51) Int. Cl.
*A61B 17/34* (2006.01)

(52) U.S. Cl.
USPC ....... 604/168.01; 604/272; 604/274; 604/900

(58) Field of Classification Search
USPC .............. 604/168.01, 166.01, 900, 272, 274
See application file for complete search history.

(56) References Cited

U.S. PATENT DOCUMENTS

| | | | |
|---|---|---|---|
| 5,478,328 A * | 12/1995 | Silverman et al. | 604/272 |
| 5,649,911 A | 7/1997 | Trerotola | |
| 5,868,699 A * | 2/1999 | Woodruff et al. | 604/506 |
| 6,221,056 B1 | 4/2001 | Silverman | |
| 6,340,359 B1 | 1/2002 | Silverman | |
| 6,391,014 B1 | 5/2002 | Silverman | |
| 7,037,296 B2 * | 5/2006 | Kadziauskas et al. | 604/294 |
| 8,172,802 B2 * | 5/2012 | Wiley | 604/164.06 |
| 2008/0154217 A1 * | 6/2008 | Carrez et al. | 604/272 |

* cited by examiner

*Primary Examiner* — Nicholas Lucchesi
*Assistant Examiner* — Benjamin Koo
(74) *Attorney, Agent, or Firm* — Welsh Flaxman & Gitler LLC (57) ABSTRACT

A hypodermic needle minimizing resistance to catheter advancement during vascular cannulation includes a needle shaft and a needle tip including an open needle bevel extending along middle and proximal portions of the open bevel until a distal end of the needle shaft, wherein a most distal portion of the open bevel is filled to prevent flashback. The hypodermic needle also includes a catheter overlying the needle shaft in the resting position.

1 Claim, 2 Drawing Sheets

PRIOR ART

FIG. 3

MINIMIZING RESISTANCE TO CATHETER ADVANCEMENT DURING VASCULAR CANNULATION

CROSS REFERENCE TO RELATED APPLICATION

This application claims the benefit of U.S. Provisional Application Ser. No. 61/421,135, entitled "Specially Configured Matched Needle/Catheter Combinations to Improve Vessel/Catheter Engagement", filed Dec. 8, 2010, which is incorporated herein by reference.

BACKGROUND OF THE INVENTION

1. Field of the Invention

The invention relates to minimizing resistance to catheter advancement during vascular cannulation.

2. Description of the Related Art

The high incidence of obtaining flashback via the needle but failing to thread the overlying catheter ("flashback yes/threading no") is largely responsible for the reported incidence of 2.6 attempts for each successful intravenous (IV) catheter insertion. Failure to thread is attributable, in large part, to the difficulties encountered threading the catheter through a vessel wall.

Figure 1:
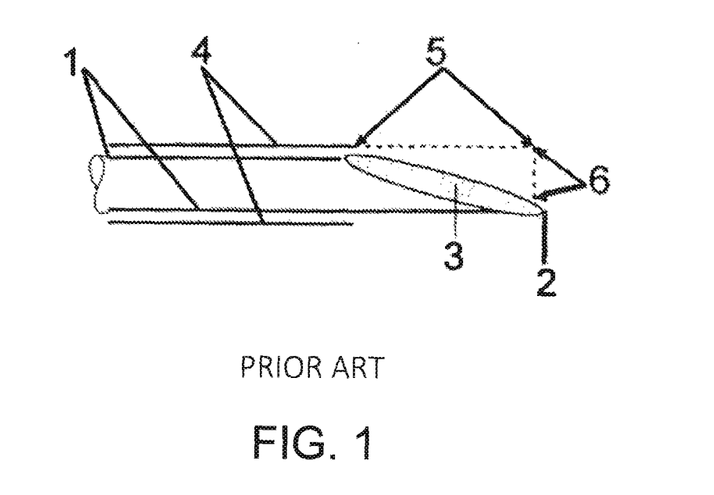
FIG. 1 is a side view of standard hypodermic needle showing: standard needle shaft 1; standard needle tip 2; standard open needle bevel extending from the tip along the entire taper, until the distal end of the shaft 3; standard catheter overlying needle shaft in the resting position 4; distance (between arrows) between most distal point of potential flashback and end of catheter on shaft, thereby constituting the potential distance that a catheter may be advanced with the dotted portion being free-hanging 5; and maximum potential distance (between arrows) between free-hanging portion of advancing catheter and circumference of needle at the time of flashback via the needle if catheter is advanced while needle is fixed in this position 6.

FIG. 1 shows the features of currently available (prior art) needle/catheter combinations that are predispose to such difficulty: a) the catheter may still be outside the vessel wall at the time the needle opening is within the vessel and flashback has been obtained; b) the path in the anterior vessel wall through which the catheter must be thread is much smaller than the circumference of the catheter if only the needle tip and/or distal taper have passed through the vessel wall (since they are less wide than the shaft and overlying catheter). As those skilled in the art will appreciate, the "flashback-to-catheter" distance between the open needle bevel and the end of the catheter proximal to the needle bevel is critical; the longer this distance, the greater the likelihood that the catheter will not be in the vessel lumen (or within the anterior vessel wall) at the time of flashback.

At the time of flashback, the aforementioned scenario is most common. However, needle/vessel relationships at the time of flashback may range from:

1) At one extreme (cited above), only the narrow needle tip, with its open bevel, may be within the vessel. Threading of the overlying catheter through the anterior wall of the vessel would be prone to problems.
2) At the other extreme, the tip of the needle may have passed through the vessel lumen to the posterior wall of the vessel, while part of the bevel remains within the vessel. Threading would be impeded by the posterior vessel wall.

It often is not clear which we way to go when the catheter initially fails to thread; i.e., should one advance the needle so as to increase vascular entry (to correct #1 above); should one withdraw the assembly from the distal wall (to correct #2 above)? A mistake is not only time-consuming; it can lead to catheter damage (burring, bending) and possible vessel trauma and, clearly, failed insertion.

Between the two extremes, the open needle bevel and tip may lie within the vessel lumen while the proximal bevel and/or all or part of the needle taper and/or the distal needle shaft (and overlying catheter) may undesirably be outside or within the vessel wall (as opposed to being within the vessel lumen). Hence the flashback-to-catheter distance is critical.

Thus, failure to thread an intravascular catheter despite attainment of flashback via the underlying needle is often the consequence of "a matter of millimeters:"

- is the catheter appropriately in the vessel?
- are the needle and catheter a few mm too far into the vessel such that catheter threading is inhibited by abutment against the distal vessel?
- is the catheter a few mm short of the vessel even though the needle is intravascular?
- is the path created by the needle in the anterior wall of the vessel too narrow?

The answer typically is obtained by trial and error.

As noted above, in the aforementioned needle/vessel relationships, there not only is a difference in catheter location at the time of flashback, but also the size of the needle portion that has passed through the anterior vessel wall and hence size of the path along which the catheter must thread in the anterior wall of the vessel:

1) If only the narrow needle tip has reached the vessel, the path within the vessel wall likely would be relatively narrow since only a relatively narrow portion of the needle's distal taper would have passed through the anterior wall and thereby created a channel within said wall.
2) If the tapered region proximal to the tip reached the vessel, the path width would correspond to the changing width of the taper and thus range in caliber between the width of the taper and the width of the shaft.
3) If the shaft is fully within or through the vessel wall, then the path will conform to the circumference of the needle shaft (and allow for easiest threading through the anterior wall).

The impact of these factors (e.g., the encumbrance of difficult catheter insertion and potentially bending the hanging end of the catheter as it advanced through the narrow path created by the needle taper and point) can best be appreciated by picturing what is occurring at the level of the skin (where it is readily visible). As it passes through the skin, the catheter remains adjacent to the needle shaft of the needle and there is no freely hanging catheter. However, if the a catheter is thread over a guidewire of significantly smaller circumference, then the catheter will get "hung up" at the skin unless a slit is made in the skin (with a knife—not practical for a vessel "hidden" under the skin and prone to injury and bleeding).

Catheter/Vessel Relationships

As discussed above in relation to FIG. 1, and as shown in U.S. Provisional Application Ser. No. 61/421,135, which is incorporated herein by reference, since the catheter that overlies the needle traditionally ends proximal to the proximal end of the needle's open bevel and taper, the catheter typically is not engaged with the vessel at the time that flashback via the needle initially is detected. Hence, the catheter will need to be advanced over the needle to enter the vessel. Catheter advancement over the shaft should be relatively simple for a catheter adjacent to a shaft which has created a channel in the vessel wall (that obviously is the circumference of the shaft). However, advancing the catheter through the vessel wall is more complicated when the catheter must be advanced if the needle taper and tip (as opposed to shaft) are in the anterior vessel wall:

- this not only would result in a freely hanging catheter end as the catheter is advanced beyond the needle shaft (due to the gap between the circumference of the needle tip and taper vs. the catheter);
- but also requires catheter advancement through a path whose circumference is much smaller than that of the catheter.

Both factors predispose to impedance to catheter advancement through the vessel wall and the potential for bending or otherwise damaging the catheter tip.

As noted above, the problem, and hence the solution, lies within a ~1-5 mm span on the needle/catheter combination; specifically, the flashback-to-catheter distance shown in FIG. 1. This distance for a given needle/catheter combination is relatively constant for a given needle gauge in that current combinations have a catheter which ends uniformly (i.e., without a slant conforming to the needle bevel) slightly proximal to a traditional bevel. It is easy to appreciate why modification of this configuration is critical in light of the aforementioned statements as to the importance of the location of the catheter at the time of flashback and the size of the path created by the needle in the vessel wall.

Attempts to Overcome the Problem—Needles with Recessed Orifice(s)

Attempts to overcome the problem posed by the flashback-to-catheter gap have focused primarily on the use of recessed orifices (e.g., a closed-tip pencil point needle with a recessed orifice on the needle and overlying catheter). However, this comes at potential "cost":

- unless specifically modified (as described in U.S. Provisional Application Ser. No. 61/421,135), the point of a pencil-point needle has the sharpness of a pencil (as opposed to a hypodermic needle);
- it requires a change of insertion technique (since pencil points require a different angle of insertion);
- it may require a greater length of insertion (to reach the recessed orifice), which may compromise catheter threading as there is increased likelihood that threading will be impeded by the posterior vessel wall (one inventor (Wiley et al.) proposed curving the back wall of the needle to minimize penetration of the distal wall of the vessel (it is believed this would further compromise the ability to pierce the skin and penetrate the vessel)); and
- if the catheter is lengthened so as to reach an orifice on the needle shaft, then it likely would either be narrowed at its distal end, markedly slanted and/or freely hanging over the needle region of lesser circumference.

Clearly, if a needle cannot enter the vessel, then ease of catheter threading becomes moot.

In U.S. Pat. No. 5,478,328 (in 1996), the inventors of the present application appreciated the potential for using a recessed-orifice pencil-point needle for catheter insertion. However, although it was mentioned that a catheter could be threaded, the main purpose of the catheter was to cover the orifices to minimize contamination. Additionally, a problem in the present context, the relative bluntness of a pencil-point needle was advantageous for needles designed to decrease the likelihood of causing healthcare worker injury. Specifically, in U.S. Pat. No. 5,478,328, the inventors of the present application recommended pencil point needles for healthcare worker safety in part because they are less sharp than standard hypodermic needles.

In U.S. Pat. No. 6,391,014, Silverman showed that puncturing the skin with a pencil-point needle requires more pressure than with a standard open-bevel hypodermic needle. During testing as shown in FIGS. 31 and 32 of the '014 patent, Silverman found that "a standard open-bevel needle consistently punctured the skin such that blood appeared (and pain was felt) at 9-10 mm Hg pressure. (Lesser forces, due to lower currents, did not cause skin puncture.) In contrast, a sharp closed tip (pencil-point) needle required a pressure of >15 mmHg to puncture the skin (and this was to a depth which did not advance the orifice into the skin)."

FIGS. 31 and 32 from Silverman (U.S. Pat. No. 6,391,014) shows means I've provided for testing needle sharpness. FIGS. 31a and 31b illustrate a device for determining the force required for a given needle to penetrate the skin (FIG. 31a) or a diaphragm (FIG. 31b) wherein the needle is mounted on a scale which records the force required for penetration. FIGS. 32a and 32b illustrate a more elaborate means of testing the penetrability of skin and diaphragms. The illustrated mechanism is designed to provide involuntary movements of the thumb by contraction of the adductor pollicis muscle as a result of stimulation of the ulnar nerve (analogous to the means used to assess neuromuscular weakness in patients undergoing general anesthesia). The force of contraction is recorded by a transducer (specifically an adductor pollicis force transducer). In the pictured embodiments, the needle is maintained in a fixed position in front of the thumb. In alternative embodiments, the needle can be secured to a thumb while the object to be punctured is maintained in a fixed position in front of it. During testing with the setup illustrated in FIG. 32, we found that a standard open-bevel needle consistently punctured the skin such that blood appeared (and pain was felt) at 9-10 mm Hg pressure. (Lesser forces, due to lower currents, did not cause skin puncture.) In contrast, a sharp closed tip needle required a pressure of >15 mmHg to puncture the skin (and this was to a depth which did not advance the orifice into the skin).

In addition to the recessed-orifice, pencil-point needle, another configuration for a recessed orifice needle had been proposed. In 1997, Tretola introduced an embodiment that provided a solid, beveled needle tip joined to a straight cylindrical body with a side hole proximally spaced from, but near the tip. The hole is carried on the needle body and the adjacent overlying catheter wall, near its distal end. This hole enables flashback to occur after the catheter has fully penetrated the vessel. However, this has not gained widespread acceptance and has been criticized by Wiley et al. (filed patent application, 2010) because "the use of a solid tip dictates that the needle be inserted a significant distance into the vessel before any flashback occurs. This degree of insertion may, in fact, be excessive. In addition, the tip is constructed with the traditional bevel, having a point residing in line with the sidewall. In other words, the tip and point are simply extensions of the bottom side of the cylindrical needle shaft, and thus the structure of the needle still invites over-insertion as set forth in FIG. 2 [of Wiley] above." The risk of over-insertion is, in fact, enhanced by the relatively proximal placement of the side hole. Moreover, the traditional beveled tip does nothing to reduce the damage potential from an over-penetrating insertion."

SUMMARY OF THE INVENTION

It is, therefore, an object of the present invention to provide a method and apparatus for improve catheter threading and potential limitations by providing needle catheter embodiments which achieve one or both of the following:

1) eliminate the flashback-to-catheter distance and thereby achieve at least partial entry of the end of the catheter into the vessel lumen at the time of flashback through the needle (—this has been the objective of needles with a recessed orifice and a catheter extending to or beyond said orifice as per Silverman/Kniffin December 2010 provisional);
2) facilitate catheter advancement through the vessel wall by either:

reducing the flashback-to-catheter distance so that the catheter is within the vessel wall at the time of flashback through the needle;

altering the needle/catheter configuration so that the path in the vessel wall through which the catheter will be thread is of sufficient caliber (i.e., that it has not simply been created by the narrow needle tip). [Note—many of our proposed embodiments introduced herein are designed to achieve this aim]

In accordance with the implementation of the present invention, the goals are achieved while avoiding:

increased difficulty of insertion due to decreased needle sharpness, altered steepness or length of the needle taper, and/or changed angle of insertion by the operator features [which may hinder the use of conical (pencil-point) needles].

significant compromise of flashback via the needle that would impede detection of the needle's being intravascular;

causing the operator to advance the needle to an otherwise excessive degree within the vessel lumen [(as would occur with a needle with a markedly recessed the needle opening (e.g., a markedly recessed orifice)]

significantly compromising detection of flashback by limiting flow (by excessively reducing the size of the opening or placing the orifice so that, even when it is within the vessel lumen, it is too small and/or abuts against the vessel wall).

the need to markedly narrow the end of the catheter (and thus compromise its channel) so as to remain adjacent to the needle taper place the catheter at significantly increased risk for bending, developing burrs or other injury (as a consequence of creating a weakened region or a free-standing "hanging" region that extends beyond the needle shaft on the given side and must course through a vessel wall that doesn't have a suitably wide path).

The inventors have also found that if a recessed-orifice closed-tip construction is utilized to promote catheter-vessel engagement prior to flashback, then closed-tip needles are needed that avoid making healthcare providers change needle insertion technique (e.g. change angle of insertion, insert with increased pressure).

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 2 is a side view of an inventive hypodermic needle embodiment wherein the distal portion. of the bevel is filled. so that the distal tip is solid. As shown in. FIG. 1, the hypodermic needle includes a needle shaft 101; a needle tip of inventive embodiment 102; an open needle bevel of inventive embodiment, extending along the middle and proximal portions: of the tip until the distil end of the shaft. The most distal portion of the bevel is filled to prevent flashback via this region 103; a catheter overlying needle shaft in the resting position 104; a distance (between arrows) between. most distal point of potential flashback on inventive embodiment and end of catheter on shaft, thereby constituting the potential distance that a catheter may be advanced with the dotted portion being free-hanging 105; a maximum. potential distance (between arrows)between free-hanging portion of advancing catheter and circumference of needle at the time of flashback via the needle 106; and a filled region of distal tip in accordance with invention. The distance between arrows delineates a representative degree of filling, thereby identifying the distance the inventive needle would need to be advanced into vessel before it is possible to obtain flashback 107.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

In light of the encumbrances inherent to the use of a conical (pencil point) needle for penetrating a blood vessel as discussed above, the present invention provides structures functioning more akin to the standard hypodermic needle used for catheter insertion (open bevel, sharp tip).

Our goal with the embodiments summarized in Tables I and II is to decrease the flashback-to-catheter distance so as to achieve at least one of the following:

Engagement of the catheter within the vessel lumen at the time of flashback.

Engagement of the catheter within the anterior vessel wall at the time of flashback.

Creation of a path with >50% diameter of the catheter by the time of flashback as a minimum efficacy standard when vessel/catheter engagement has not yet been achieved. This entails ensuring that flashback cannot occur until a region of the taper with greater than the prescribed width has passed through the anterior vessel wall (even if the catheter has not yet reached the anterior wall). Otherwise:

there may be a region of undesirably unsupported freestanding catheter as the catheter is advanced and the gap between the outside of the needle taper and the overlying catheter is >50% of the catheter diameter; the catheter thus would be more prone to being bent or otherwise damaged while the catheter is breaching the vessel wall to enter the vessel lumen;

the path through the vessel wall is unacceptably narrow.

An objective of the embodiments of the invention introduced herein is to ensure that less "force" is required to thread the catheter, thereby making "happy catheters" with less hang-ups (at the vessel wall) so that the catheter end is not "bent out of shape" or otherwise injured. Achieving such an improvement even when the catheter has not reached the vessel by the time of needle flashback potentially is a product of two factors, both of which are attributable to having a wider path in the vessel wall at the time of catheter threading:

a) Entering the vessel wall—It's a matter of millimeters.

Less of a gap between the catheter and the caliber of the needle portion that created the opening and path in the anterior vessel wall, since said gap can lead to complications due to a hanging portion of the catheter and hence between the catheter and the circumference of the path within the vessel wall. Clinicians typically rely on open-bevel needles within an open-ended catheter that ends approximately ~2 to 7 mm proximal to the needle tip and ~0.5 to 3 mm proximal to the proximal end of the open bevel. (Distance depends on size of the needle, most notably its gauge and associated bevel length). Even if blood is flowing through the needle, little, if any, of the catheter is within the vessel until one advances the needle so that a portion of the shaft (ranging from approximately at least 0.5 mm to ~3 mm proximal to the proximal end of the bevel) is within the vessel.

b) Threading through the vessel wall—It's a matter of physics.

Resistance within a tubular structure is inversely proportional to the $4^{th}$ power of the radius. Hence, doubling the radius of a tube reduces its resistance by $2^4=16$ fold. Admittedly, passage of a catheter through a path in the wall of a vessel is not the same as flowing liquid through a tube. However, the relationship holds with respect to the fact that a wider path through the vessel wall poses less resistance to threading of a catheter into the vessel.

Inventive Needle (Summarized in Table I)

In accordance with preferred embodiments and as discussed herein, the present invention provides a hypodermic needle for penetration of tissues (such as skin and blood vessel wall) and/or penetrable diaphragms (e.g., on top of penetrable bottle tops and stoppers) designed for a requisite degree of advancement prior to fluid delivery or withdrawal via said needle. The needle has a standard shaft with a throughbore that terminates at the distal end as an open bevel. The needle tip is biased in a manner equal to or comparable to that of a standard hypodermic needle such no change in insertion pressure or angulation is required. The needle is modified so that the standard open bevel is filled at its distal end so that contact of the open portion of the bevel with the conduit (e.g., vessel) lumen or bottle interior is "delayed" until penetration is sufficient for the open bevel to be exposed to the fluid within said vessel, container or conduit. The opening is still on the needle end (i.e., not recessed from a solid tip). The opening is still sufficiently large to enable efficient flow of fluid via the needle. The width of the needle within the vessel wall or diaphragm is wider than would be the case if simply the needle tip were through said vessel wall or diaphragm.

Still further, the needle is matched with an overlying catheter that covers the shaft of the needle until deliberate advancement beyond the needle tip such that the solid needle tip delays flashback via the needle until the open portion of the bevel is exposed to blood within the vessel. The distance between the point of flashback via the needle and the end of the catheter overlying the needle shaft ("flashback-to-catheter distance") is reduced; i.e., the catheter is therefore advanced closer to the vessel lumen at the time of flashback so as to accomplish at least one of the following: the circumference of the portion of the angled needle taper within the vessel wall more closely approaches that of the overlying the uniform diameter catheter so as to facilitate catheter advancement into the vessel; and the overlying catheter has reached the vessel wall by the time flashback via the needle is obtained.

The above is accomplished without significantly compromising needle sharpness or angle of insertion. In addition, it may offer a safety component in that the solid tip will not house inoculum which could infect a healthcare worker exposed to an inadvertent needle stick. (This may expand the value of this invention by decreasing health care worker risk during injections, insertion of needles into diaphragms (bottle tops, intravenous infusion sets). Although the present inventive needle is distinct from my prior disclosures (U.S. Pat. Nos. 5,478,328, 6,221,056, 6,340,359 and 6,391,014) many of the applications of the safety needles described therein are applicable to the present inventive needle design. The extent necessary, the disclosures of U.S. Pat. Nos. 5,478,328, 6,221, 056, 6,340,359 and 6,391,014, are incorporated herein by reference.

The components of the common theme related above can best be achieved if the open bevel needle is modified so that it has a solid tip which ensures that a prescribed distance (e.g., ~2-5 mm) is in the vessel before flashback occurs. This "delay" of flashback ensures that more of the needle has advanced through the anterior vessel wall by the time of flashback.

Recommended Dimensions:

The basic dimensions, that is, the angle, length and circumference are dependent in part on gauge of the given needle/catheter combination, which in turn is influenced in part by vessel size, vessel wall thickness (e.g., artery vs vein) and clinical requirements. The prescribed distance will be influenced by the thickness of the vessel wall(s).

Figure 2:
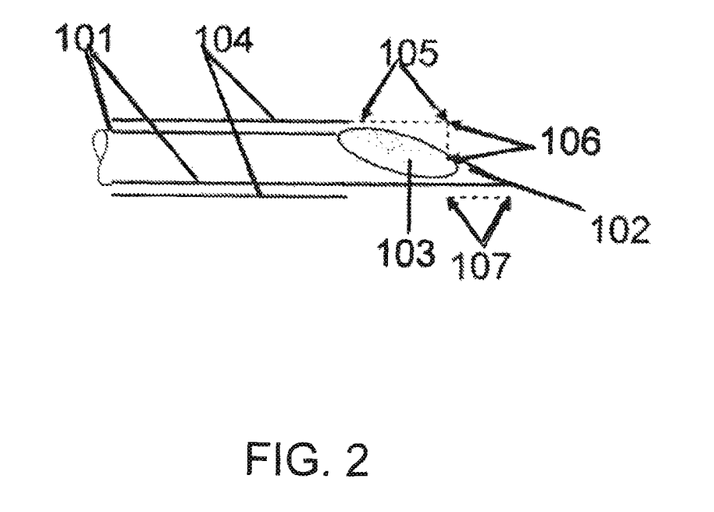
Figure 3:
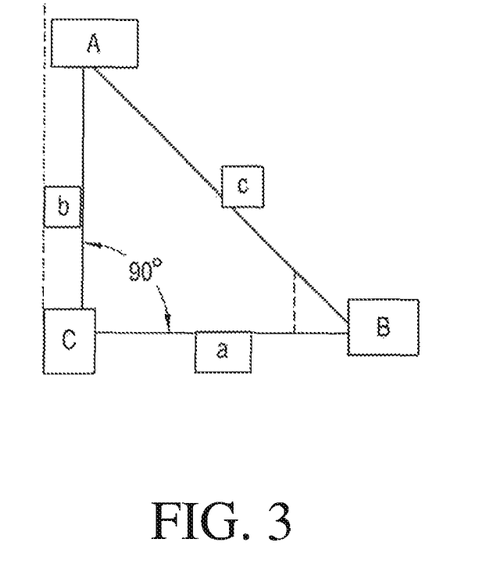
FIG. 3 is a schematic of a triangle used in describing the inventive concept.

Referring now to FIG. 3, this triangle is oriented as per FIGS. 1 and 2 (toward the end of this document such that "B" represents the needle tip and line "a" represents the standard flat side of the needle. Point C can be viewed as point of the needle that is just outside vessel wall when the needle tip has entered the vessel. In a standard needle/catheter combination, the catheter likely would still be outside the vessel wall and would have to pass over this region to enter the vessel. Line c shows the taper of the needle bevel for this distance along the needle taper. Line b shows the diameter of the needle at point C (i.e., diameter of the needle taper that is just outside the vessel wall at the time the needle tip reaches the vessel lumen). The dotted lines show how this would be shifted by an inventive solid tip such that the diameter of the needle (b) just outside the vessel wall at the time when flashback is wider than in the traditional needle.

Assuming an angle of 45 degrees at point B: and that the normal distance between B and C is 5 mm, then "delaying" flashback by 3 mm (to dotted line near B) would result in a widening of dotted line b from the standard 5 mm to an inventive 8 mm. This would be consistent with inventive aims including, widening of the needle channel and reduction of the flashback to catheter distance.

Such filling (deliberately creating of "dead space" which enables "normal" needle insertion without flashback) can have at least one of the following benefits:

1. decreased flashback-to-catheter distance; if this is matched with a catheter modification (discussed in subsequent section), this can ensure engagement of the catheter within the vessel lumen (or at least within the wall) at the time of flashback
2. sufficient advancement of the needle through the vessel wall such that the prescribed requirements for caliber of the path within the wall are met since a wider portion of the needle has passed through wall than would be accomplished by the prior art.
3. It also provides potentially valuable information to the operator: at the time of flashback, the user knows that the solid distal tip already has entered the vessel. Additionally, if one withdraws a traditional needle slightly, it is possible to exit the vessel and "blow the vein" because of the hole in its wall. Not so with the inventive needle because of the added distance beyond the opening.

Requirements for Size of Distal Opening:

When part of the standard open bevel is filled in this manner, we must ensure that we continue to meet the following criteria:

Must be sufficient to enable flashback.

% of an opening that can be blocked (e.g., replaced by solid needle) will depend on the size of the opening of given needle without the inventive blocking component; e.g., if it is determined that an orifice can be no smaller that provided by a standard 24 ga needle, then a 22 gauge needle should not be blocked more than a predetermined percentage.

Options to Maintain Adequate Opening ("◊") for Flashback

It is contemplated the options for maintaining the adequate opening for flashback may be achieved by lengthening the open bevel (by decreasing its angle with the distal end) so that, with the distal region occluded, there still is a sufficient caliber orifice for detection of flashback. It is also contemplated the options for maintaining the adequate opening for flashback may be achieved by widening the open bevel so as to increase the area encompassed by the decreased length of open bevel.

Additional Description of Needle Embodiments

It is appreciated the filling of the needle tip may be provided such that, within a desired distance (e.g. ~0.2 mm) of most distal potential needle site of flashback, the circumference of the needle is >50% of the circumference of its shaft (and hence the overlying catheter). Considering the prior art, it is possible that flashback can be obtained within ~1 mm of needle entry into the vessel; at this point it is likely that only a very narrow portion of the taper is within the vessel wall (which can range in width from ~0.5 to ~3.0 mm in diameter). A primary objective of this invention is to ensure that a portion of the needle that is 50-100% of needle shaft diameter is within the vessel.

This can be accomplished by filling in distal region (1 to 5 mm) of open distal tip and/or slightly changing the length of the tip as with a solid tip extension, so long as the objective is met to ensure that the open bevel starts at a wider portion of the taper.

For example, and also considering the discussion above with regard to FIG. 3, assuming a traditional bevel angle of 45°, increasing the amount to which the flat end of the bevel is within the vessel (and obviously through the anterior vessel wall) from 1 mm to 3 mm would ensure that the circumference of the path in the vessel wall would be proportionally greater than would be in the prior art.

FIGS. 3 and 4 in our U.S. Provisional Patent Application Ser. No. 61/421,135 show how one can restrict the needle opening to the mid and/or proximal portions of the needle end. FIG. 2 of the present disclosure shows the impact compared to that of a standard hypodermic needle (FIG. 1).

Inventive Modifications of the Catheter (Summarized in Table II)

The aforementioned needle modifications which decrease flashback-to-catheter distance can be coupled with changes in the overlying catheter that further decrease the flashback-to-catheter distance by lengthening all or, in most embodiments, part of the catheter with the expressed goal of:

increasing the likelihood of catheter engagement in the vessel lumen at the time of flashback via the needle. Inventive catheter modifications can do so by extending the catheter toward the needle tip and thereby eliminating the flashback-to-catheter distance between the needle opening and all or part of the catheter end; and/or increasing the likelihood of and degree of catheter engagement in the vessel wall at the time of flashback via the needle (i.e., within ~1-3 mm of the lumen). Inventive catheter modifications can shorten the flashback-to-catheter distance by extending all or part of the catheter toward the needle tip and thereby further decreasing the flashback-to-catheter distance between the needle opening and all or part of the catheter end.

In the description of inventive needle embodiments discussed above, we emphasized the importance of taper circumference within the vessel wall being >50% of the catheter circumference so as to ensure adequate size of the path made by the needle in the vessel wall. We now also emphasize that this is important so as to provide a suitable foundation for the distal end of the catheter wherein the part of the catheter overlying the circumference of the needle taper maintains its normal circumference (while the remainder of the catheter ends proximal to the needle bevel (in its "normal" position encircling the needle shaft). The catheter may be slanted or alternatively contoured so as to maximize the amount of suitably supported catheter that is advanced along the intact circumference of the needle taper.

The embodiments described herein seek to avoid what we deem to be measurably unacceptable features:

Markedly narrowing the distal end of the catheter so as to conform to an underlying tapered needle region Slanting or otherwise shaping the catheter end so that it has a free-hanging flimsy region that is prone bending or other injury.

In preferred embodiments, catheter is slanted so that none is free hanging in the "resting state" and <50% of the catheter circumference has the potential to be free-hanging and potentially having to be thread via a path in the vessel wall that is less than 50% of the catheter circumference.

Slanting to such a degree that it predisposes to part of the catheter being extravascular after threading into the vessel.

Extending a portion of catheter so that it is freely hanging over the needle in catheter's unadvanced state and/or advanced position Note—The undesirable potential for freely hanging in either the unadvanced or advanced position will be mitigated by the needle shaft in the vessel wall being at least 50% of the shaft (and hence catheter) circumference. Hangups during advancement can be further reduced by rotating the catheter once the longer distal end is engaged so that the shorter end now benefits from the support of the needle circumference.

Embodiments for Catheter Modification Include:

slanting wherein the most distal end of the catheter (1-7 mm longer) can be supported by a sufficient width of needle to avoid undesirable features that predispose to flimsy and/or freely overhanging sections and wherein such slanting can enable:

a portion of the catheter to be within the vessel lumen at the time of flashback a portion of the catheter to be within the path created by the underlying needle within the anterior vessel wall other catheter configurations (e.g., U-shaped and V-shaped) that achieve comparable outcomes Examples of slanting and of the U- and V-shapes are shown in FIGS. 16, 19 and 21 of our U.S. Provisional Patent Application Ser. No. 61/421,135).

TABLE I

Potential Inventive Embodiments - Needles:

1. Unchanged*
2. Modified with a recessed orifice (not the focus of the present disclosure; see our U.S. Provisional Patent Application Ser. No. 61/421,135)
3. Modified by creation of a solid tip - e.g., by "filling in" ~distal third of the open bevel - (instead of prior art continuation of open bevel to the tip) to delay flashback upon insertion of the needle into a vessel and thereby:
    a. shorten flashback-to-catheter distance so as to ensure catheter is intraluminal or within the anterior vessel wall when flashback through the needle is obtained; and/or
    b. provide wider needle taper circumference at level of open bevel (i.e., a level of flashback) to:
        i. provide wider surface to support extended portion of catheter; and/or
        ii. ensure that at least the prescribed minimal width (e.g., >50% of shaft circumference) of path in the anterior vessel wall has been created by the needle by the time of flashback (so as to facilitate catheter threading through the vessel wall).
4. Optional widening (or lengthening) of middle section of the bevel proximal to the solid (filled) distal portion so as to maximize flashback despite replacement of distal bevel with solid tip
5. Optional widening of proximal section of bevel so as to maximize flashback despite replacement of distal bevel with solid needle
6. Optional groove (or nub) matched with catheter to promote rotation of catheter upon advancement
so that, once long end of catheter is intravascular, the short end of catheter is advanced over solid needle as opposed to open bevel.

TABLE II

Potential Inventive Embodiments - Catheters

1. Unchanged*
2. Modified to combine with needle that contains a recessed orifice(s) (not the focus of the present disclosure; see our U.S. Provisional Patent Application Ser. No. 61/421,135)
3. Modified so that a portion of the catheter extends distally along the taper closer to the site of needle flashback
    a. Slanted
    b. Otherwise modified (e.g., U-shaped or V-shaped as shown our U.S. Provisional Patent Application Ser. No. 61/421,135) to provide region that is more distal (and thus to be within the vessel lumen or anterior wall) than portion of the catheter that is proximal to the needle bevel
4. Optional nub (or groove) matched with needle to promote rotation of catheter upon advancement so that, once long end of catheter is intravascular, short end of catheter is advanced over solid needle as opposed to open bevel.

*clearly, combination of unchanged needle and unchanged catheter is not part of this invention.

Figures

FIG. 1. Side view of standard hypodermic needle showing:
1. Standard needle shaft
2. Standard needle tip
3. Standard open needle bevel extending from the tip along the entire taper, until the distal end of the shaft
4. Standard catheter overlying needle shaft in the resting position
5. Distance (between arrows) between most distal point of potential flashback and end of catheter on shaft, thereby constituting the potential distance that a catheter may be advanced with the dotted portion being free-hanging
6. Maximum potential distance (between arrows) between free-hanging portion of advancing catheter and circumference of needle at the time of flashback via the needle if catheter is advanced while needle is fixed in this position.

FIG. 2. Side view of an inventive hypodermic needle embodiment wherein the distal portion of the bevel is filled so that the tip is solid.

101. Needle shaft
102. Needle tip of inventive embodiment
103. Open needle bevel of inventive embodiment, extending along the middle and proximal portions of the taper until the distal end of the shaft. The most distal portion of the bevel is filled to prevent flashback via this region
104. Catheter overlying needle shaft in the resting position
105. Distance (between arrows) between most distal point of potential flashback on inventive embodiment and end of catheter on shaft, thereby constituting the potential distance that a catheter may be advanced with the dotted portion being free-hanging.
106. Maximum potential distance (between arrows) between free-hanging portion of advancing catheter and circumference of needle at the time of flashback via the needle.
107. Filled region of distal taper in accordance with invention. The distance between arrows delineates a representative degree of filling, thereby identifying the distance the inventive needle would need to be advanced into vessel before it is possible to obtain flashback.

The invention claimed is:

1. A hypodermic needle minimizing resistance to catheter advancement during vascular cannulation, comprising:
a needle shaft having a needle tip;
the needle tip extending to a distal point in alignment with a longitudinal axis extending along a wall of the needle shaft, the needle tip including an open needle bevel extending diametrically across a full extent of the needle, an open portion of the open needle bevel extending along middle and proximal portions of the open needle bevel until a distal end of the needle shaft, wherein a most distal portion of the open needle bevel is filled so that contact of the open portion of the open needle bevel with a vessel is delayed until approximately 2-5 mm of the needle tip is in the vessel to delay flashback from the open portion of the open needle bevel, the open needle bevel being filled as dead space to ensure that flashback cannot occur until a region of the open needle bevel with greater than a prescribed width has passed through an anterior vessel wall;

a catheter having a constant diameter along, its length, the catheter overlying the needle shaft in the resting position;

wherein a distance from the catheter to a distal tip of the open needle bevel is greater than a distance from the catheter to a most distant point of flashback via the open portion of the open needle bevel, thereby delaying flashback until approximately 2-5 mm of the needle tip is in the vessel to ensure an adequate size path is formed in a vessel wall so as to minimize resistance to advancement of the catheter during vascular cannulation.

* * * * *

UNITED STATES PATENT AND TRADEMARK OFFICE
CERTIFICATE OF CORRECTION

PATENT NO. : 8,465,457 B2
APPLICATION NO. : 13/314885
DATED : June 18, 2013
INVENTOR(S) : David G. Silverman and Sally A. Kniffin It is certified that error appears in the above-identified patent and that said Letters Patent is hereby corrected as shown below:

In the Claims

Column 12, line 51, cancel the text beginning with "1. A hypodermic" to and ending "vascular cannulation" in column 13, line 13, and insert the following claim:

1. A hypodermic needle minimizing resistance to catheter advancement during vascular cannulation, comprising: a needle shaft having a needle tip; the needle tip extending to a distal point in alignment with a longitudinal axis extending along a wall of the needle shaft, the needle tip including an open needle bevel extending diametrically across a full extent of the needle, an open portion of the open needle bevel extending along middle and proximal portions of the open needle bevel until a distal end of the needle shaft, wherein a most distal portion of the open needle bevel is filled so that contact of the open portion of the open needle bevel with a vessel is delayed until approximately 2-5 mm of the needle tip is in the vessel to delay flashback from the open portion of the open needle bevel, the open needle bevel being filled as dead space to ensure that flashback cannot occur until a region of the open needle bevel with greater than a prescribed width has passed through an anterior vessel wall; a catheter having a constant diameter along its length, the catheter overlying the needle shaft in the resting position; wherein a distance from the catheter to a distal tip of the open needle bevel is greater than a distance from the catheter to a most distant point of flashback via the open portion of the open needle bevel, thereby delaying flashback until approximately 2-5 mm of the needle tip is in the vessel to ensure an adequate size path is formed in a vessel wall so as to minimize resistance to advancement of the catheter during vascular cannulation.

Signed and Sealed this
Thirtieth Day of July, 2013

Teresa Stanek Rea
*Acting Director of the United States Patent and Trademark Office*